(12) United States Patent
Matsubara et al.

(10) Patent No.: US 11,332,687 B2
(45) Date of Patent: May 17, 2022

(54) FRICTION ADJUSTING AGENT AND LUBRICATING OIL COMPOSITION

(71) Applicant: Idemitsu Kosan Co.,Ltd., Chiyoda-ku (JP)

(72) Inventors: Kazushige Matsubara, Chiba (JP); Hiroaki Koshima, Chiba (JP); Toshiaki Iwai, Chiba (JP); Hideki Kamano, Chiba (JP)

(73) Assignee: Idemitsu Kosan Co..Ltd., Chiyoda-ku (JP)

( * ) Notice: Subject to any disclaimer, the term of this patent is extended or adjusted under 35 U.S.C. 154(b) by 0 days.

(21) Appl. No.: 16/625,997

(22) PCT Filed: Apr. 12, 2018

(86) PCT No.: PCT/JP2018/015312
§ 371 (c)(1),
(2) Date: Dec. 23, 2019

(87) PCT Pub. No.: WO2019/003573
PCT Pub. Date: Jan. 3, 2019

(65) Prior Publication Data
US 2021/0095221 A1    Apr. 1, 2021

(30) Foreign Application Priority Data

Jun. 30, 2017   (JP) .............................. JP2017-128455

(51) Int. Cl.
*C10M 133/44*        (2006.01)
*C07D 207/40*        (2006.01)
(Continued)

(52) U.S. Cl.
CPC ......... *C10M 133/44* (2013.01); *C07D 207/40* (2013.01); *C10M 169/04* (2013.01);
(Continued)

(58) Field of Classification Search
CPC ............ C07D 207/412; C10M 133/44; C10M 133/16; C10M 2215/086; C10N 2030/06;
(Continued)

(56) References Cited

U.S. PATENT DOCUMENTS

| 5,942,472 A * | 8/1999 | Watts .................. | C10M 133/56 |
| | | | 508/291 |
| 2004/0192562 A1* | 9/2004 | Morita ................ | C10M 163/00 |
| | | | 508/185 |

(Continued)

FOREIGN PATENT DOCUMENTS

| EP | 0 889 112 A1 | 1/1999 |
| GB | 1 318 874 | 5/1973 |
| JP | 49-24064 | 6/1974 |
| JP | 9-202890 A | 8/1997 |
| JP | 2005-325355 A | 11/2005 |
| JP | 2009-518804 A | 5/2009 |
| JP | 2010-530470 A | 9/2010 |

(Continued)

OTHER PUBLICATIONS

International Search Report dated Jul. 3, 2018 in PCT/JP2018/015312 filed on Apr. 12, 2018, citing references AB-AF, AM-AV, and AX-AY therein, 3 pages.

Singh et al., "Abilities of Some Compounds to Stabilize Mahwa Oil from High Temperature Oxidative Degradation for Biolubricant Applications", Waste and Biomass Valorization, 2014, vol. 5, No. 5, pp. 847-855.

(Continued)

*Primary Examiner* — Vishal V Vasisth
(74) *Attorney, Agent, or Firm* — Oblon, McClelland, Maier & Neustadt, L.L.P.

(57) ABSTRACT

The present invention provides a compound represented by formula (1) (in formula (1), $R^1$ and $R^2$ each independently represent a group represented by formula (2) or $NHR^0$ (where $R^1$ and $R^2$ are not simultaneously $NHR^0$), $R^0$ represents any one of hydrogen, an alkyl group having 1-20 carbon atoms, an alkenyl group having 2-30 carbon atoms, an aryl group having 6-30 carbon atoms, an alkylaryl group having 7-30 carbon atoms, and an arylalkyl group having 7-30 carbon atoms, each $R^3$ independently represents hydrogen or a hydrocarbon group having 1-30 carbon atoms, l represents an integer of 0-4, m represents an integer of 1-4 (where m is an integer of 2-4 in the case where $R^1$ and $R^2$ are a group represented by formula (2)), and each n independently represents an integer of 0-4, and, in formula (2), $R^4$ represents a hydrocarbon group having 6-24 carbon atoms, and $X^1$ and $X^2$ each independently represent an oxygen atom or a sulfur atom).

11 Claims, No Drawings

(51) Int. Cl.
    *C10M 169/04*    (2006.01)
    *C10N 40/04*    (2006.01)

(52) U.S. Cl.
    CPC ... *C10M 2203/003* (2013.01); *C10M 2215/30* (2013.01); *C10N 2040/045* (2020.05)

(58) Field of Classification Search
    CPC ........ C10N 2040/042; C10N 2040/045; C10N 2030/76
    See application file for complete search history.

(56) References Cited

U.S. PATENT DOCUMENTS

| | | |
|---|---|---|
| 2005/0250656 A1 | 11/2005 | Ishikawa et al. |
| 2007/0060484 A1 | 3/2007 | Singh et al. |
| 2010/0137173 A1 | 6/2010 | Sheets et al. |
| 2011/0028364 A1 | 2/2011 | Shrestha et al. |
| 2013/0029890 A1 | 1/2013 | Shanker et al. |
| 2015/0376538 A1 | 12/2015 | Manabe et al. |

FOREIGN PATENT DOCUMENTS

| | | |
|---|---|---|
| JP | 2011-46938 A | 3/2011 |
| JP | 2012-158721 A | 8/2012 |
| JP | 2014-210883 A | 11/2014 |
| WO | WO 2014/136911 A1 | 9/2014 |

OTHER PUBLICATIONS

Inoue et al., "Effects of Interaction between Engine Oil Additives on Solubilization and Adsorption", J. Japan Petrol. Inst., Sekiyu Gakkaishi, 1982, vol. 25, No. 2, pp. 106-111.

\* cited by examiner

FRICTION ADJUSTING AGENT AND LUBRICATING OIL COMPOSITION

This application is a 371 of PCT/JP2018/015312, filed Apr. 12, 2018.

TECHNICAL FIELD

The present invention relates to a compound having the effect of reducing friction, a friction adjusting agent and a lubricating oil composition.

BACKGROUND ART

As transmissions to be used for automobiles, metal belt-type, chain-type, toroidal-type or another type continuously variable transmissions have been developed. In continuously variable transmissions, power transmission is performed by a friction coefficient between a belt or chain and a pulley, and for this reason, lubricating oils for automatic transmissions to be used for them are required to have a friction coefficient between metals at a certain level or higher.

The lubricating oil must transmit power while protecting a friction surface with an oil film formed on a sliding portion. Accordingly, the lubricating oil must have a certain friction coefficient, and the improvement of the friction coefficient is particularly desired in fields requiring energy saving. However, when the lubricating oil has a high friction coefficient between metals, noise resistance is low. Specifically, there is a trade-off relationship between a high friction coefficient between metals and noise resistance, but a lubricating oil, wherein both the two values are good, and a friction adjusting agent constituting the lubricating oil are desired.

As a continuously variable transmission oil required to achieve a balance between frictional force and noise resistance, a lubricating oil composition, which contains a base oil of a lubricating oil and a succinimide compound, and which satisfies a specific friction coefficient between metals and shudder prevention lifetime, is disclosed (Patent Document 1: International Publication WO2014/136911 pamphlet).

PRIOR ART DOCUMENTS

Patent Documents

Patent Document 1: International Publication WO2014/136911 pamphlet

SUMMARY OF THE INVENTION

Problems to be Solved by the Invention

However, the lubricating oil composition described in Patent Document 1 is not sufficient from the viewpoint of recent severer demand for achieving a balance between the friction coefficient between metals and noise resistance. In particular, in the case of chain-type continuously variable transmissions, a noise tends to be more easily generated when compared to belt-type continuously variable transmissions, and for this reason, lubricating oil compositions are strongly desired to achieve a balance between the friction coefficient and noise resistance, but there was no friction adjusting agent or lubricating oil composition sufficiently satisfying the demand.

The present invention was made in consideration of the above-described circumstances, and a friction adjusting agent and lubricating oil composition having a high friction coefficient between metals and high noise resistance were obtained.

Means for Solving the Problems

The present inventors diligently made researches in order to solve the above-described problems and achieved the present invention by synthesizing a compound represented by formula (1) (Compound 1) and using the compound for a friction adjusting agent and a lubricating oil composition. Specifically, the present invention is as described below.

[1] A compound represented by formula (1):

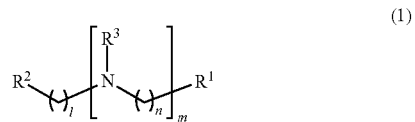

wherein in formula (1):

$R^1$ and $R^2$ each independently represent a group represented by formula (2) or $NHR^0$ (where $R^1$ and $R^2$ are not simultaneously $NHR^0$);

$R^0$ represents any one of hydrogen, an alkyl group having 1 to 20 carbon atoms, an alkenyl group having 2 to 30 carbon atoms, an aryl group having 6 to 30 carbon atoms, an alkylaryl group having 7 to 30 carbon atoms, and an arylalkyl group having 7 to 30 carbon atoms;

each $R^3$ independently represents hydrogen or a hydrocarbon group having 1 to 30 carbon atoms;

l represents an integer of 0 to 4;

m represents an integer of 1 to 4 (where m is an integer of 2 to 4 in the case where $R^1$ and $R^2$ are a group represented by formula (2)); and each n independently represents an integer of 0 to 4,

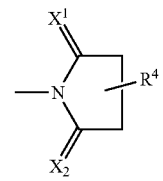

and wherein in formula (2):

$R^4$ represents a hydrocarbon group having 6 to 24 carbon atoms; and $X^1$ and $X^2$ each independently represent an oxygen atom or a sulfur atom.

[2] A friction adjusting agent comprising the compound according to item [1].

[3] A lubricating oil composition comprising a base oil and the friction adjusting agent according to item [2].

[4] A lubricating oil composition for continuously variable transmissions comprising a base oil and the friction adjusting agent according to item [2].

[5] A gear shifting method using the lubricating oil composition for continuously variable transmissions according to item [4].

Advantageous Effect of the Invention

A preferred embodiment of the present invention provides a friction adjusting agent having a high friction coefficient between metals and high noise resistance.

BEST MODE FOR CARRYING OUT THE INVENTION

Hereinafter, embodiments of the present invention will be described in detail. Note that the present invention is not limited to the below-described embodiments and can be arbitrarily changed and then carried out without departing from the gist of the present invention.

1. Compound 1

Compound 1 of the present invention is a compound represented by formula (1) above.

In formula (1), $R^1$ and $R^2$ each independently represent a group represented by formula (2) or $NHR^0$, but $R^1$ and $R^2$ are not simultaneously $NHR^0$. When $R^1$ and $R^2$ are simultaneously $NHR^0$, it is difficult to achieve a balance between a high friction coefficient between metals and high noise resistance.

Each $R^3$ independently represents hydrogen or a hydrocarbon group having 1 to 30 carbon atoms. When $R^3$ is a hydrocarbon group having more than 30 carbon atoms, noise resistance is poor. Each $R^3$ independently represents preferably hydrogen, an alkyl group having 6 to 24 carbon atoms, an alkenyl group having 6 to 24 carbon atoms, an aryl group having 6 to 24 carbon atoms, an alkylaryl group having 7 to 24 carbon atoms, an alkenylaryl group having 7 to 24 carbon atoms, an arylalkyl group having 7 to 24 carbon atoms or an arylalkenyl group having 7 to 24 carbon atoms, more preferably hydrogen, an alkyl group having 10 to 22 carbon atoms, an alkenyl group having 10 to 22 carbon atoms, an aryl group having 10 to 22 carbon atoms, an alkylaryl group having 11 to 22 carbon atoms, an alkenylaryl group having 11 to 22 carbon atoms, an arylalkyl group having 11 to 22 carbon atoms or an arylalkenyl group having 11 to 22 carbon atoms, and particularly preferably hydrogen, an alkyl group having 10 to 22 carbon atoms or an alkenyl group having 10 to 22 carbon atoms.

$R^0$ represents hydrogen, an alkyl group having 1 to 20 carbon atoms, an alkenyl group having 2 to 30 carbon atoms, an aryl group having 6 to 30 carbon atoms, an alkylaryl group having 7 to 30 carbon atoms or an arylalkyl group having 7 to 30 carbon atoms. When it is not the above-described functional group, solubility in a base oil is poor. $R^0$ represents preferably hydrogen, an alkyl group having 1 to 15 carbon atoms, an alkenyl group having 2 to 15 carbon atoms or an aryl group having 6 to 15 carbon atoms, and more preferably hydrogen, an alkyl group having 1 to 10 carbon atoms or an alkenyl group having 2 to 10 carbon atoms.

Further, in formula (2), $R^4$ represents a hydrocarbon group having 6 to 24 carbon atoms. When it is a hydrocarbon group having less than 6 carbon atoms, solubility in a base oil is poor, and when it is a hydrocarbon group having more than 24 carbon atoms, noise resistance is poor. $R^4$ preferably represents an alkyl group having 6 to 24 carbon atoms, an alkenyl group having 6 to 24 carbon atoms, an aryl group having 6 to 24 carbon atoms, an alkylaryl group having 7 to 24 carbon atoms, an alkenylaryl group having 7 to 24 carbon atoms, an arylalkyl group having 7 to 24 carbon atoms or an arylalkenyl group having 7 to 24 carbon atoms. $R^4$ represents more preferably an alkyl group having 10 to 22 carbon atoms or an alkenyl group having 10 to 22 carbon atoms, and particularly preferably an alkyl group having 14 to 20 carbon atoms or an alkenyl group having 14 to 20 carbon atoms.

In formula (2), $X^1$ and $X^2$ each independently represent an oxygen atom or a sulfur atom.

Examples of the alkyl group include various alkyl groups having a linear-chain, branched-chain or ring structure. Examples of the alkyl group having a ring structure include a cycloalkyl group, an alkylcycloalkyl group and a cycloalkylalkyl group. Examples of the cycloalkyl group include a cycloalkyl group having 5 to 7 carbon atoms such as a cyclopentyl group, a cyclohexyl group and a cycloheptyl group. Further, the substitution position on the cycloalkyl ring is optional.

Examples of the alkenyl group include various alkenyl groups having a linear-chain, branched-chain or ring structure. Examples of the alkenyl group having a ring structure include a cycloalkenyl group, an alkylcycloalkenyl group, an alkenylcycloalkyl group, a cycloalkenylalkyl group and a cycloalkenylalkenyl group. The cycloalkyl group is as described above. Examples of the cycloalkenyl group include a cycloalkenyl group having 5 to 7 carbon atoms such as a cyclopentenyl group, a cyclohexenyl group and a cycloheptenyl group. Further, the substitution positions on the cycloalkenyl ring and the cycloalkyl ring are optional.

Examples of the aryl group include phenyl and naphthyl (having a hydrocarbyl substituent). Further, in the above-described alkylaryl group, alkenylaryl group, arylalkyl group and arylalkenyl group, the substitution position with respect to the aryl group is optional.

Examples of the alkylaryl group include o-tolyl, m-tolyl, p-tolyl, 2,3-xylyl, 2,4-xylyl, 2,5-xylyl, o-cumenyl, m-cumenyl, p-cumenyl and mesityl.

Examples of the arylalkyl group include benzyl, phenethyl, diphenylmethyl, triphenylmethyl, 1-naphthylmethyl, 2-naphthylmethyl, 2,2-diphenylethyl, 3-phenylpropyl, 4-phenylbutyl and 5-phenylpentyl.

Further, in formula (1), l represents an integer of 0 to 4, preferably an integer of 0 to 3, more preferably an integer of 1 to 3, and particularly preferably an integer of 2 to 3.

In formula (1), m represents an integer of 1 to 4, but in the case where $R^1$ and $R^2$ are a group represented by formula (2), m is an integer of 2 to 4. When m in formula (1) exceeds 4, solubility in a base oil is poor, and in addition, the friction coefficient between metals is low and noise resistance is poor. Further, since high solubility in a base oil, a high friction coefficient between metals and high noise resistance are obtained, m is preferably an integer of 2 to 3, and in the case where $R^1$ and $R^2$ are a group represented by formula (2), m is preferably an integer of 2 to 3.

Since solubility is reduced when m and n in formula (1) are large, n+m is preferably 1 to 6, more preferably 1 to 5, and particularly preferably 3 to 5.

In this specification, "the number of amino groups" refers to the sum of the value of m in formula (1) and the number of $NHR^0$ of the end groups ($R^1$, $R^2$).

In the present invention, the number of amino groups in Compound 1 represented by formula (1) is preferably 1 to 5, more preferably 1 to 4, and particularly preferably 2 to 4 from the viewpoint of achieving the balance between solubility in a base oil, a high friction coefficient between metals and noise resistance.

2. Synthesis of Compound 1

The method for producing Compound 1 of the present invention is not particularly limited, but for example, it can be synthesized as described below.

As shown in formulae (α) and (β) below, Compound 1 can be obtained by an imidization reaction between a compound of formula (A) such as 2-hydrocarbyl succinic anhydride and a compound of formula (B) such as diethylenetriamine.

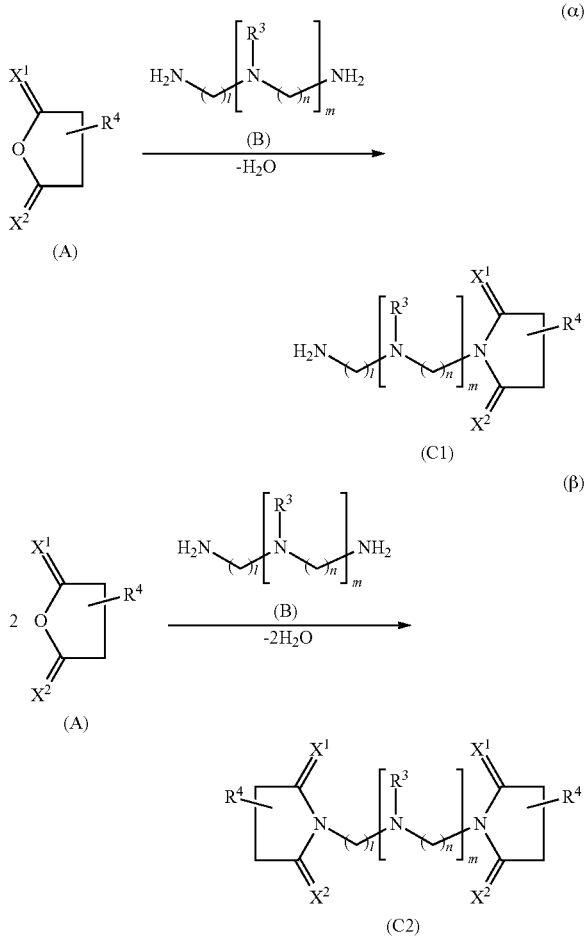

(In formulae (A), (C1) and (C2) above, $R^4$, $X^1$ and $X^2$ are the same as $R^4$, $X^1$ and $X^2$ in formula (2), and in formulae (B), (C1) and (C2) above, $R^3$, l, m and n are the same as $R^3$, l, m and n in formula (1).)

Specifically, to an organic solvent solution (e.g., xylene solution) of the compound of formula (B), an organic solvent solution (e.g., xylene solution) of the compound of formula (A) is added dropwise while stirring, and the mixture is further stirred. After that, the mixture is heated to about 150° C. and stirred, and subjected to xylene reflux, thereby synthesizing Compound 1 such as a succinimide compound. In this case, it is preferred to gradually reduce the pressure using a diaphragm pump to completely distill away purified water or xylene under reduced pressure.

2-hydrocarbyl succinic anhydride is commercially available, but in order to obtain an acid anhydride having a specific structure, synthesis may be conducted according to the publicly-known method described in Patent Document 1 (International Publication WO2014/136911 pamphlet).

3. Friction Adjusting Agent

The friction adjusting agent of the present invention is a composition comprising Compound 1 of the present invention.

The content of Compound 1 of the present invention in the friction adjusting agent of the present invention is not particularly limited, but from the viewpoint of achieving the balance between a high friction coefficient between metals and noise resistance, the content is preferably 50% by mass or more, more preferably 80% by mass or more, and even more preferably 90% by mass or more, and may be 100% by mass based on the total amount of the friction adjusting agent.

4. Lubricating Oil Composition

The lubricating oil composition of the present invention is a composition comprising a base oil and the friction adjusting agent of the present invention, and may further comprise other components.

(Base Oil)

The base oil contained in the lubricating oil composition of the present invention is not particularly limited, and any material may be suitably selected from among mineral oils and synthetic oils which are conventionally used as a base oil of a lubricating oil.

Examples of mineral oils include those obtained by a method in which: a crude oil is subjected to atmospheric distillation to obtain an atmospheric residue; it is subjected to vacuum distillation to obtain a lube-oil distillate; and it is subjected to at least one treatment selected from among solvent deasphalting, solvent extraction, hydrocracking, solvent dewaxing, catalytic dewaxing, hydrotreating, etc. to perform purification. Examples of mineral oils also include those produced by isomerizing a wax or GTL WAX (gas-to-liquid wax). Among them, a mineral oil treated by means of hydrotreating is preferred.

Examples of synthetic oils include poly-α-olefins such as polybutene and an α-olefin homopolymer or copolymer (e.g., ethylene-α-olefin copolymer), esters such as polyol ester, dibasic acid ester and phosphoric acid ester, ethers such as polyphenylether, polyglycol, alkylbenzene, and alkylnaphthalene. Among these synthetic oils, poly-α-olefins and esters are particularly preferred, and materials obtained by combining these two types of materials are also preferably used as synthetic oils.

In one embodiment of the present invention, as the base oil, the above-described mineral oils may be used solely, or two or more of them may be used in combination. Further, the above-described synthetic oils may be used solely, or two or more of them may be used in combination. Moreover, at least one of the above-described mineral oils may be used in combination with at least one of the above-described synthetic oils.

The content of the base oil contained in the lubricating oil composition of the present invention is not particularly limited, but it is preferably 60% by mass or more, more preferably 70% by mass to 98% by mass, and even more preferably 70% by mass to 95% by mass.

(Friction Adjusting Agent)

The friction adjusting agent contained in the lubricating oil composition of the present invention is a composition comprising Compound 1 of the present invention.

The content of the friction adjusting agent in the lubricating oil composition of the present invention is not particularly limited, but from the viewpoint of the matter that the kinetic viscosity of the composition becomes not too high, solubility in the base oil and a high friction coefficient between metals, the content is preferably 0.05% by mass to 5% by mass, more preferably 0.1% by mass to 4% by mass, and even more preferably 0.05% by mass to 2% by mass.

Further, the nitrogen content (N content) in the friction adjusting agent is preferably 100 mass ppm to 3000 mass ppm, more preferably 150 mass ppm to 2500 mass ppm, and particularly preferably 200 mass ppm to 2000 mass ppm based on the total amount of the lubricating oil composition.
(Other Components)

The lubricating oil composition of the present invention may further comprise other components to an extent that does not inhibit the effect of the present invention. Examples of the other components include additives usually used in lubricating oils such as an extreme pressure agent, a cleaning agent, a viscosity index improver, a pour point depressant, an abrasion preventing agent, an ashless dispersant, a corrosion inhibitor, a metal deactivator, a defoaming agent and an antioxidant.

Examples of the extreme pressure agent include phosphorus compounds such as (mono, di or tri-thio) phosphates (phosphites) and zinc dithiophosphate, and sulfur-containing compounds such as disulfides, sulfurized olefins, sulfurized oils and fats and dithiocarbamates. When the antiwear agent is contained in the lubricating oil composition of the present invention, the content thereof is preferably 0.005% by mass to 5% by mass based on the total amount of the lubricating oil composition.

Examples of the cleaning agent include an alkali metal sulfonate, an alkaline earth metal sulfonate, an alkali metal phenate, an alkaline earth metal phenate, an alkali metal salicylate, an alkaline earth metal salicylate and a mixture thereof. These cleaning agents may be overbased. When the cleaning agent is contained in the lubricating oil composition of the present invention, the content thereof is not particularly limited. However, when it is for an automatic transmission or continuously variable transmission, usually, the content is preferably 0.01% by mass to 5% by mass based on the total amount of the lubricating oil composition on the metal element equivalent basis.

Examples of the viscosity index improver include polymethacrylate (PMA)-based materials (e.g., polyalkyl methacrylate, polyalkyl acrylate, etc.), olefin-based copolymer (OCP)-based materials (e.g., an ethylene-propylene copolymer (EPC), polybutylene, etc.), and styrene-based copolymers (e.g., polyalkyl styrene, a styrene-diene copolymer, a styrene-isoprene copolymer, a styrene-diene hydrogenated copolymer, a styrene-maleic anhydride ester copolymer, etc.). The PMA-based viscosity index improver includes dispersant and non-dispersant ones. The dispersant PMA-based viscosity index improver is a homopolymer of alkyl methacrylate or alkyl acrylate, and the non-dispersant PMA-based viscosity index improver is a copolymer of alkyl methacrylate or alkyl acrylate and a polar monomer having dispersibility (e.g., diethylaminoethyl methacrylate, etc.). Further, like the PMA-based viscosity index improver, the OCP-based viscosity index improver includes non-dispersant and dispersant ones.

The mass average molecular weight (Mw) of these viscosity index improvers is usually 5,000 to 1,000,000, and in the case of the PMA-based viscosity index improver, the mass average molecular weight (Mw) is preferably 20,000 to 300,000, more preferably 25,000 to 250,000, and particularly preferably 25,000 to 200,000. Further, in the case of the OCP-based viscosity index improver, the mass average molecular weight (Mw) is preferably 5,000 to 800,000, and more preferably 10,000 to 500,000.

These viscosity index improvers may be used solely, or two or more of them may be used in combination. From the viewpoint of the improvement of the viscosity index, the blending amount thereof is preferably 0.5% by mass or more, more preferably 0.7% by mass or more, and particularly preferably 1.0% by mass or more based on the total amount of the lubricating oil composition. Further, the blending amount is preferably 15% by mass or less, more preferably 10% by mass or less, and even more preferably 9.5% by mass or less.

Examples of the pour point depressant include an ethylene-vinylacetate copolymer, a condensate of chlorinated paraffin and naphthalene, a condensate of chlorinated paraffin and phenol, polymethacrylate (PMA)-based materials (polyalkyl methacrylate, polyalkyl acrylate, etc.), polyalkyl styrene, polyvinyl acetate and polybutene, and PMA-based materials are preferably used. Note that the PMA-based pour point depressant has a chemical structure similar to that of the above-described PMA-based viscosity index improver, but with respect to the pour point depressing action, it is considered that a side chain alkyl group forming an ester bond with the main chain of PMA is cocrystallized with the wax content of the base oil of the lubricating oil to adjust the direction of crystal growth to change the crystal form of wax, thereby depressing the pour point. The mass average molecular weight of the PMA-based pour point depressant is, for example, 10,000 to 150,000.

These pour point depressants may be used solely, or two or more of them may be used in combination. The blending amount thereof is preferably 0.01% by mass or more, and more preferably 0.10% by mass or more, while it is preferably 10% by mass or less, more preferably 5.0% by mass or less, and even more preferably 1.0% by mass or less based on the total amount of the lubricating oil composition.

Examples of the abrasion preventing agent include a sulfur-based abrasion preventing agent such as a thiophosphoric acid metal salt (examples of the metal: zinc (Zn), lead (Pb) and antimony (Sb)) and a thiocarbamic acid metal salt (an example of the metal: zinc (Zn)), and a phosphorus-based abrasion preventing agent such as a phosphoric acid ester (e.g., tricresyl phosphate). These abrasion preventing agents may be used solely, or two or more of them may be used in combination. The blending amount of the abrasion preventing agent is preferably 0.05% by mass to 5.0% by mass based on the total amount of the lubricating oil composition.

Examples of the ashless dispersant include benzylamines and boron-containing benzylamines. These ashless dispersants may be used solely, or two or more of them may be used in combination.

The blending amount of the ashless dispersant is preferably 0.10% by mass to 20% by mass, and more preferably 0.3% by mass to 10% by mass based on the total amount of the lubricating oil composition.

Examples of the corrosion inhibitor include: alkyl or alkenyl succinic acid derivatives such as dodecenylsuccinic acid half ester, octadecenylsuccinic anhydride and dodecenylsuccinamide; fatty acid soap; alkyl sulfonate; polyhydric alcohol partial esters such as sorbitan monooleate, glycerin monooleate and pentaerythritol monooleate; amines such as rosin amine and N-oleylsarcosine; dialkyl phosphite amine salts; fatty acid amides; oxidized paraffin; and alkylpolyoxyether. These corrosion inhibitors may be used solely, or two or more of them may be used in combination.

The blending amount of the corrosion inhibitor is preferably 0.01% by mass to 3.0% by mass based on the total amount of the lubricating oil composition.

Examples of the metal deactivator (examples of the metal: copper and iron) include benzotriazole, triazole derivatives, benzotriazole derivatives and thiadiazole derivatives. These metal deactivators may be used solely, or two or more of them may be used in combination.

The blending amount of the metal deactivator is preferably 0.01% by mass to 5.0% by mass based on the total amount of the lubricating oil composition.

Examples of the defoaming agent include silicone compounds such as dimethylpolysiloxane; and ester-based compounds such as polyacrylates. These defoaming agents may be used solely, or two or more of them may be used in combination.

The blending amount of the defoaming agent is preferably 0.05% by mass to 5.0% by mass based on the total amount of the lubricating oil composition.

As the antioxidant, a hindered phenol-based or amine-based antioxidant, zinc alkyldithiophosphate (ZnDTP) or the like is preferably used. As the hindered phenol-based antioxidant, bisphenol-based or ester group-containing phenol-based antioxidants are preferred. As the amine-based antioxidant, dialkyl diphenylamine or naphthylamine-based antioxidants are preferred. These antioxidants may be used solely, or two or more of them may be used in combination.

The blending amount of the antioxidant is preferably 0.05% by mass to 7.0% by mass based on the total amount of the lubricating oil composition.

5. Method for Producing Lubricating Oil Composition

The method for producing the lubricating oil composition of the present invention is not particularly limited, but the composition can be obtained by mixing components to be contained in the lubricating oil composition (base oil, friction adjusting agent and other components).

6. Intended Use of Lubricating Oil Composition

The compound represented by formula (1), the friction adjusting agent and the lubricating oil composition of the present invention are suitably used, for example, for automotive transmissions and other transmissions, and particularly suitably used for a lubricating oil composition to be used for continuously variable transmissions (e.g., metal belt-type/chain-type continuously variable transmissions, etc.).

EXAMPLES

Production Example 1 (Bisimide N=3)

To a 200 ml separable flask equipped with a Dean-Stark condenser tube, a nitrogen injection tube and a thermometer, 18.9 g (0.1 mmol) of tetraethylenepentamine and 30 ml of xylene were fed to prepare a xylene solution 1. Meanwhile, in a conical flask, 70.1 g (0.2 mmol) of isooctadecenylsuccinic anhydride and 30 ml of xylene were mixed homogeneously to prepare a xylene solution 2. To the xylene solution 1, the xylene solution 2 of isooctadecenylsuccinic anhydride was added dropwise while stirring over 30 minutes. The mixture was heated to 100° C. and stirred for 1 hour, and then the mixture was further heated to 150° C. and stirred while being subjected to xylene reflux for 4 hours to obtain about 1.8 g of generated water. The nitrogen gas was stopped, and the pressure was gradually reduced to 0.02 MPa using a diaphragm pump to nearly completely distill away the generated water and the solvent xylene. Subsequently, the pressure was reduced to 2 mmHg using a vacuum pump to completely distill away the generated water and the solvent xylene. The temperature was decreased to 80° C. and nitrogen was added to obtain atmospheric pressure, thereby obtaining an objective substance, bisimide composed of tetraethylenepentamine and isooctadecenylsuccinic acid.

Production Example 2 (Monoimide N=2)

The operation was carried out in a manner similar to that in Production Example 1, except that 20.6 g (0.2 mmol) of diethylenetriamine was used instead of 18.9 g (0.1 mmol) of tetraethylenepentamine, and an objective substance, monoimide composed of diethylenetriamine and isooctadecenylsuccinic acid was obtained. Note that the amount of the generated water obtained when the temperature was increased to 150° C. and xylene reflux was performed was about 3.6 g.

Hereinafter, the present invention will be described in detail by way of working examples, but the technical scope of the present invention is not limited thereto.

[Evaluation Methods]

The evaluation methods employed in the Examples and Comparative Examples are as described below.

(Friction Coefficient Between Metals)

To a low-speed sliding testing machine specified in JASO M349:2010, a fixture to which 3 metal pins were attached was attached, and it was rubbed against a metal plate to evaluate the friction coefficient between metals. The test conditions for the measurement of the friction coefficient between metals were as described below.

Test Apparatus
  Material of metal pins: SUJ2
  Material of metal plate: SUJ2
Test Conditions:
  Oil temperature: 120° C.
  Rotation speed: 200 rpm
  Load: 3600 N (Noise Resistance)

A value obtained by dividing a friction coefficient at a rotation speed of 10 rpm by a friction coefficient at a rotation speed of 200 rpm ($\mu 10/\mu 200$) was referred to as a "$\mu$ ratio". The friction coefficient at a rotation speed of 10 rpm was measured under the same conditions as those for the measurement of the friction coefficient between metals except for the rotation speed. For example, in the case where the $\mu$ ratio is less than 1, when the rotation speed is increased, the friction coefficient between metals increases, and for this reason, the noise is reduced. Meanwhile, in the case where the $\mu$ ratio is more than 1, when the rotation speed is increased, the friction coefficient between metals decreases, and for this reason, the noise is increased. Accordingly, the lower the $\mu$ ratio is, the better the noise resistance is.

Examples 1-2 and Comparative Examples 1-3

In Examples 1-2 and Comparative Examples 1-3 described below, Comparative Example 1 is a reference example showing the standards of the friction coefficient between metals and noise resistance. Specifically, lubricating oil compositions having a higher friction coefficient between metals and a lower $\mu$ ratio compared to Comparative Example 1 (reference example) are in the Examples, and the others are in Comparative Examples 2 and 3.

Components were mixed based on the formulation compositions shown in Table 1 to prepare lubricating oil compositions. The friction adjusting agent used in Example 1 is the bisimide compound produced in Production Example 1, and the friction adjusting agent used in Example 2 is the monoimide compound produced in Production Example 2.

The results regarding the friction coefficient between metals ($\mu 200$) and the $\mu$ ratio ($\mu 10/\mu 200$) representing noise resistance of these lubricating oil compositions are shown in Table 1.

TABLE 1

| | | | Unit | Example 1 | Example 2 | Comparative Example 1 | Comparative Example 2 | Comparative Example 3 |
|---|---|---|---|---|---|---|---|---|
| Formulation composition | Base oil | Hydrocracked mineral oil (kinetic viscosity at 100° C.: 2.67 mm$^2$/s) | % by mass | 77.24 | 77.58 | 78.15 | 71.82 | 76.86 |
| | Viscosity index improver | Polymethacrylate (Mw: 3.0 × 10$^4$) | % by mass | 16.00 | 16.00 | 16.00 | 16.00 | 16.00 |
| | Cleaning agent | High base number Ca sulfonate TBN: 300 mgKOH/g | % by mass | 0.40 | 0.40 | 0.40 | 0.40 | 0.40 |
| | Extreme pressure agent | Dilauryl hydrogen phosphite | % by mass | 0.05 | 0.05 | 0.05 | 0.05 | 0.05 |
| | | Acidic phosphoric acid ester amine salt | % by mass | 0.05 | 0.05 | 0.05 | 0.05 | 0.05 |
| | | Oleyl acid phosphate | % by mass | 0.10 | 0.10 | 0.10 | 0.10 | 0.10 |
| | Antioxidant | DTTP | % by mass | 0.30 | 0.30 | 0.30 | 0.30 | 0.30 |
| | | Dithiocarbamate | % by mass | 0.15 | 0.15 | 0.15 | 0.15 | 0.15 |
| | | Monobutylphenyl-monooctylphenylamine | % by mass | 0.30 | 0.30 | 0.30 | 0.30 | 0.30 |
| | Friction adjusting agent | Bisimide composed of tetraethylenepentamine and isooctadecenylsuccinic acid, N = 3 | % by mass | 0.91 | — | — | — | — |
| | | Monoimide composed of diethylenetriamine and isooctadecenylsuccinic acid, N = 2 | % by mass | — | 0.57 | — | — | — |
| | | Polybutenylsuccinic bisimide, N = 2, PIB Mw 2300 | % by mass | — | — | — | 6.33 | — |
| | | Isooctadecenylsuccinic monoimide, N = 0, polar group: hydroxy group | % by mass | — | — | — | — | 1.29 |
| | Additive package | | % by mass | 4.50 | 4.50 | 4.50 | 4.50 | 4.50 |
| | Total | | % by mass | 100.00 | 100.00 | 100.00 | 100.00 | 100.00 |
| Content of element | Calcium content in cleaning agent | | mass ppm | 500 | 500 | 500 | 500 | 500 |
| | Phosphorus content | | mass ppm | 120 | 120 | 120 | 120 | 120 |
| | Nitrogen content in friction adjusting agent | | mass ppm | 500 | 500 | 0 | 500 | 500 |
| Characteristics | Friction coefficient between metals (µ200) | | — | 0.099 | 0.101 | 0.096 | 0.102 | 0.095 |
| | µ ratio (µ10/µ200) | | — | 0.955 | 0.993 | 1.011 | 1.112 | 1.059 |

Note)
In Table 1, N respresents the number of amino groups in the compound.

As shown in Table 1, the lubricating oil composition of Example 1 in which isooctadecenylsuccinic bisimide (N=3) that is the compound represented by formula (1) was used as the friction adjusting agent and the lubricating oil composition of Example 2 in which isooctadecenylsuccinic monoimide (N=2) that is the compound represented by formula (1) was used as the friction adjusting agent had a higher friction coefficient between metals (µ200) and a lower µ ratio (µ10/µ200) when compared to the lubricating oil composition of Comparative Example 1 not containing the compound represented by formula (1).

The friction adjusting agent used in the lubricating oil composition of Comparative Example 2 is polybutenylsuccinic bisimide, and the compound is a succinic bisimide compound, but not the compound represented by formula (1). The lubricating oil composition of Comparative Example 2 had a higher friction coefficient between metals (µ200) and a higher µ ratio (µ10/µ200) when compared to the lubricating oil composition of Comparative Example 1.

Further, the friction adjusting agent used in the lubricating oil composition of Comparative Example 3 is isooctadecenylsuccinic monoimide, but not the compound represented by formula (1). The lubricating oil composition of Comparative Example 3 had a lower friction coefficient between metals (µ200) and a higher µ ratio (µ10/µ200) when compared to the lubricating oil composition of Comparative Example 1.

INDUSTRIAL APPLICABILITY

The lubricating oil composition in which Compound 1 is used in the friction adjusting agent can be utilized as a transmission oil, and can be utilized as an automatic transmission oil or continuously variable transmission oil. In particular, it can be utilized as a belt-type or chain-type continuously variable transmission oil for automobiles, etc. requiring energy saving.

The invention claimed is:
1. A lubricating oil composition, comprising:
a base oil, and
0.05% by mass to 2% by mass of a friction adjusting agent comprising a compound represented by formula (1):

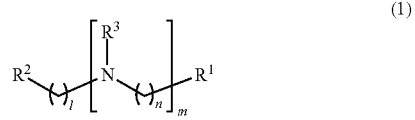

(1)

wherein in formula (1):
  $R^1$ represents a group represented by formula (2); $R^2$ represents $NHR^0$;
  $R^0$ represents hydrogen;
  each $R^3$ represents hydrogen;
  l represents an integer of 1 to 4;
  m represents an integer of 1 to 4; and
  each n independently represents an integer of 1 to 4,

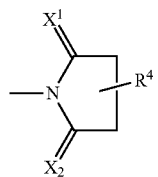

(2)

and wherein in formula (2):
  $R^4$ represents a hydrocarbon group having 10 to 22 carbon atoms and a branch in the alpha position; and
  $X^1$ and $X^2$ each represent an oxygen atom.

2. A method, comprising gear shifting a continuously variable transmission, wherein gears of the continuously variable transmission are in contact with the lubricating oil composition of claim 1.

3. The lubricating oil composition according to claim 1, wherein a nitrogen content of the friction adjusting agent is 100 ppm by mass to 3000 ppm by mass.

4. The lubricating oil composition according to claim 1, wherein a nitrogen content of the friction adjusting agent is 150 ppm by mass to 3000 ppm by mass.

5. The lubricating oil composition according to claim 1, wherein a nitrogen content of the friction adjusting agent is 200 ppm by mass to 3000 ppm by mass.

6. The lubricating oil composition according to claim 1, wherein a content of the compound represented by formula (1) in the friction adjusting agent is 50% by mass or more.

7. The lubricating oil composition according to claim 1, wherein a content of the compound represented by formula (1) in the friction adjusting agent is 80% by mass or more.

8. The lubricating oil composition according to claim 1, wherein a content of the compound represented by formula (1) in the friction adjusting agent is 90% by mass or more.

9. The lubricating oil composition according to claim 1, wherein the friction adjusting agent consists of the compound represented by formula (1).

10. The lubricating oil composition according to claim 1, wherein in formula (1):
  m represents an integer of 2 to 3.

11. The lubricating oil composition according to claim 1, wherein $R^4$ represents an alkyl group having 10 to 22 carbon atoms or an alkenyl group having 10 to 22 carbon atoms.

* * * * *